(12) United States Patent
Weeks et al.

(10) Patent No.: US 11,278,321 B2
(45) Date of Patent: Mar. 22, 2022

(54) DEVICE FOR COMPRESSING THE UTERUS

(71) Applicant: The University of Liverpool, Liverpool (GB)

(72) Inventors: Andrew Weeks, Liverpool (GB); John Porter, Wirral (GB)

(73) Assignee: The University of Liverpool, Liverpool (GB)

( * ) Notice: Subject to any disclaimer, the term of this patent is extended or adjusted under 35 U.S.C. 154(b) by 378 days.

(21) Appl. No.: 15/125,318

(22) PCT Filed: Mar. 12, 2015

(86) PCT No.: PCT/GB2015/050725
§ 371 (c)(1),
(2) Date: Sep. 12, 2016

(87) PCT Pub. No.: WO2015/136293
PCT Pub. Date: Sep. 17, 2015

(65) Prior Publication Data
US 2017/0071630 A1 Mar. 16, 2017

(30) Foreign Application Priority Data
Mar. 14, 2014 (GB) .................................. 1404614

(51) Int. Cl.
*A61B 17/42* (2006.01)
*A61B 90/00* (2016.01)
*A61B 17/12* (2006.01)

(52) U.S. Cl.
CPC .......... *A61B 17/4241* (2013.01); *A61B 17/12* (2013.01); *A61B 90/06* (2016.02);
(Continued)

(58) Field of Classification Search
CPC ..... A61B 17/4241; A61B 90/06; A61B 17/12; A61B 2090/065; A61B 2017/12004
See application file for complete search history.

(56) References Cited

U.S. PATENT DOCUMENTS 1,550,403 A * 8/1925 Newton ................. A61B 17/02
600/210
2,400,251 A * 5/1946 Nagel ................ A61B 17/4241
606/119

(Continued)

OTHER PUBLICATIONS

International Search Report and Written Opinion, European Patent Office, PCT/GB2015/050725, dated May 15, 2016, 12 pages.
(Continued)

*Primary Examiner* — Jing Rui Ou
(74) *Attorney, Agent, or Firm* — Taft Stettinius & Hollister LLP; Stephen F. Rost

(57) ABSTRACT

A device for applying a compressive force to the uterus, the device comprising a contact portion for contacting the uterus and providing a compressive force thereto, and at least two elongate handles each extending from the contact portion along a respective longitudinal axis. The at least two elongate handles are configured to facilitate insertion of the device into the body and handling of the device from outside the body when inserted. At least a part of the contact portion is configured to be radially moveable relative to the longitudinal axes between a first radial position and a second radial position where the second radial position is radially outward of the first radial position.

30 Claims, 6 Drawing Sheets

(52) U.S. Cl.
CPC ............... *A61B 2017/12004* (2013.01); *A61B 2090/065* (2016.02)

(56) References Cited

U.S. PATENT DOCUMENTS

| | | | | |
|---|---|---|---|---|
| 3,877,433 | A * | 4/1975 | Librach | A61B 1/303 606/119 |
| 4,000,743 | A * | 1/1977 | Weaver | A61B 17/4241 128/DIG. 26 |
| 5,108,408 | A * | 4/1992 | Lally | A61B 17/4241 606/119 |
| 5,250,056 | A * | 10/1993 | Hasson | A61B 17/29 606/151 |
| 5,351,679 | A * | 10/1994 | Mayzels | A61B 17/0218 600/214 |
| 5,662,676 | A * | 9/1997 | Koninckx | A61B 17/0218 600/210 |
| 10,159,596 | B2 * | 12/2018 | Tai | A61F 6/144 |
| 2004/0002702 | A1 * | 1/2004 | Xiao | A61B 18/1485 606/41 |
| 2004/0064134 | A1 * | 4/2004 | Xiao | A61B 18/02 606/21 |
| 2005/0107818 | A1 | 5/2005 | Valtchev | |
| 2007/0142750 | A1 * | 6/2007 | Kotmel | A61B 1/00091 600/587 |
| 2007/0167960 | A1 * | 7/2007 | Roth | A61B 17/0218 606/153 |
| 2007/0232913 | A1 * | 10/2007 | Lau | A61N 7/022 600/439 |
| 2008/0039865 | A1 * | 2/2008 | Shaher | A61B 17/0206 606/119 |
| 2008/0058833 | A1 * | 3/2008 | Rizvi | A61B 17/4241 606/119 |
| 2008/0249534 | A1 * | 10/2008 | Gruber | A61B 1/303 606/119 |
| 2011/0264079 | A1 | 10/2011 | Doll | |
| 2012/0172898 | A1 | 7/2012 | Pedrick | |
| 2013/0053863 | A1 * | 2/2013 | Juravic | A61B 1/303 606/119 |
| 2013/0072749 | A1 | 3/2013 | Fairneny et al. | |
| 2013/0253516 | A1 * | 9/2013 | Mackall | A61B 17/7055 606/70 |
| 2015/0127016 | A1 * | 5/2015 | Sauer | A61B 90/30 606/119 |

OTHER PUBLICATIONS

European Office Action, European Patent Office, European Patent Application No. 15710568.5, dated Nov. 21, 2017, 4 pages.

* cited by examiner

DEVICE FOR COMPRESSING THE UTERUS

This application is a U.S. national stage application under 35 U.S.C. § 371 of PCT International Application Serial No. PCT/GB2015/050725, which has an international filing date of Mar. 12, 2015, designates the United States of America, and claims the benefit of GB Application No, 1404614.8, which was filed on Mar. 14, 2014. The disclosures of each of these prior applications are hereby expressly incorporated by reference in their entirety.

FIELD OF THE DISCLOSURE

The present disclosure relates to a device for applying a compressive force to the uterus, and, in particular, to a device that may be used in the management of postpartum haemorrhage.

BACKGROUND

Postpartum haemorrhage (PPH) is responsible for around 25% of maternal mortality worldwide (WHO, 2007), reaching as high as 60% in some countries. Actual incidence rates vary across the globe but it estimated that around 14 million cases occur globally every year. Even in the UK it is still the third most common cause of maternal mortality. PPH also causes hospital morbidity. Many women require blood transfusion with approximately 1% of women with spontaneous vaginal deliveries requiring transfusion, increasing to 5% or 6% for women with instrumental deliveries or caesarean sections. Severe anaemia is another common consequence of PPH and affects about 11% of the 14 million women with PPH each year, which can result in disabling fatigue and seriously reduce a woman's capacity to look after her children and to work.

In the UK, when uterine atony (lack of tone in the uterine muscle) is the cause of the severe bleeding, the Royal College of Obstetricians and Gynecologists has developed guidance that includes a series of mechanical and pharmacological measures that should be instituted, in turn, until the bleeding stops. The first step in these measures is the implementation of bimanual uterine compression to stimulate contractions, followed by use of drugs (e.g. to induce contraction). If pharmacological measures fail to control the haemorrhage, surgical measures are implemented with intrauterine balloon tamponade being the first-line 'surgical' intervention for most women where uterine atony is the only or main cause of haemorrhage.

Bimanual compression of the uterus is an aseptic technique that involves compressing an atonic uterus between two hands, one placed internally and the other placed on the abdomen. The procedure involves introducing a gloved hand into the vagina and then forming it into a first which is placed in the anterior fornix. This hand is used to apply pressure to the anterior wall of the uterus. The other hand is used to press deeply into the abdomen, behind the fundus of the uterus in order to apply deep pressure against the posterior wall of the uterus. Compression of the uterus between the two hands is intended to be maintained until the bleeding is controlled and the uterus contracts.

It is an object of certain embodiments of the present disclosure to provide a device that assists in the management of PPH. It is an object of certain embodiments of the present disclosure to reduce the invasiveness of bimanual compression.

BRIEF SUMMARY OF THE DISCLOSURE

In accordance with an aspect of the present disclosure there is provided a device for applying a compressive force to the uterus, the device including a contact portion for contacting the uterus and providing a compressive force thereto, and at least one elongate handle extending from the contact portion along a longitudinal axis, wherein the at least one elongate handle is configured to facilitate insertion of the device into the body and handling of the device from outside the body when inserted.

At least a part of the contact portion may be configured to be radially moveable relative to the longitudinal axis between a first radial position and a second radial position where the second radial position is radially outward of the first radial position. The contact portion may be pivotally mounted so as to be radially moveable relative to the longitudinal axis, and, further, may be pivotally mounted to the at least one elongate handle.

The present disclosure may therefore permit the highly effective bimanual compression procedure to be performed in a less invasive manner. In certain circumstances, this will allow it to be used alongside pharmacological therapies at an early stage of bleeding, thus preventing ongoing blood loss and progression to surgical intervention.

The at least part of the contact portion may be rotatable relative another part of the contact portion and the longitudinal axis. Said at least part of the contact portion may be connected to another part of the contact portion by a first hinge, wherein said first hinge may be a living hinge.

Said at least part of the contact portion may comprise at least one wing portion.

The contact portion may be connected to the at least one elongate handle by a second hinge, wherein the second hinge may be a living hinge.

In certain embodiments, the device may comprise two elongate handles extending from the contact portion.

The device may be formed as a continuous elongate element that includes two living hinges spaced from one another thereby defining the contact portion that is hingedly connected to two elongate handles extending from the contact portion.

The device may further include a limiting feature for limiting the maximum insertion depth of the device in a cavity. The limiting feature may comprise a projecting portion extending radially outward from the at least one elongate handle at a predetermined distance from the contact portion, wherein the predetermined distance determines the maximum insertion depth of the device in a cavity where the opening of the cavity has a radius smaller than the radial extent of the projecting portion. The projecting portion may be a flange that is substantially circumferentially continuous about the at least one elongate handle.

The contact portion may be configured to permit the passage of fluid therethrough. The device may further include a collection reservoir for receiving fluid that passes through the contact portion. Alternatively, the device may further include one or more conduits for channeling fluid that passes through the contact portion, where the one or more conduits may extend substantially parallel to the at least one elongate handle.

The device may further include one or more sensors or indicators for measuring pressure applied by the device against a surface. The one or more sensors or indicators may form part of the contact portion. The one or more sensors or indicators may form part of the at least one elongate handle. The one or more sensors or indicators may include a mechanical indicator. The mechanical indicator may include a compressible member, where the compressible member may be a spring. The one or more sensors or indictors may include an electronic sensor.

In certain embodiments, the contact surface may be a substantially planar surface, or may be concave.

In accordance with an aspect of the present disclosure there is provided a device for applying a compressive force to the uterus, the device including a contact portion for contacting the uterus and providing a compressive force thereto, and at least two elongate handles each extending from the contact portion along a respective longitudinal axis, wherein the at least two elongate handles are configured to facilitate insertion of the device into the body and handling of the device from outside the body when inserted; wherein at least a part of the contact portion is configured to be radially moveable relative to the longitudinal axes between a first radial position and a second radial position where the second radial position is radially outward of the first radial position.

In accordance with an aspect of the present disclosure there is provided a device for applying a compressive force to the uterus, the device including a contact portion for contacting the uterus and providing a compressive force thereto, and two elongate handles each extending from the contact portion along a respective longitudinal axis, wherein the two elongate handles are configured to facilitate insertion of the device into the body and handling of the device from outside the body when inserted; wherein at least a part of the contact portion is configured to be radially moveable relative to the longitudinal axes between a first radial position and a second radial position where the second radial position is radially outward of the first radial position.

In accordance with an aspect of the present disclosure there is provided a device for applying a compressive force to the uterus, the device including a contact portion for contacting the uterus and providing a compressive force thereto, and more than two elongate handles each extending from the contact portion along a respective longitudinal axis, wherein the more than two elongate handles are configured to facilitate insertion of the device into the body and handling of the device from outside the body when inserted; wherein at least a part of the contact portion is configured to be radially moveable relative to the longitudinal axes between a first radial position and a second radial position where the second radial position is radially outward of the first radial position.

In accordance with an aspect of the present disclosure there is provided a method for treating postpartum haemorrhage, including introducing a device having a contact portion into the body of a patient; and compressing the uterus of the patient between the contact portion and an applied force external of the body.

In certain embodiments, the device includes at least one elongate handle extending from the contact portion along a longitudinal axis, and the step of compressing the uterus of the patient between the contact portion and an applied force external of the body includes applying a force to the at least one elongate handle.

In certain embodiments, a portion of the at least one elongate handle extends outside of the body when the force is applied to the at least one elongate handle.

In certain embodiments, at least a part of the contact portion is configured to be radially moveable relative to the longitudinal axis between a first radial position and a second radial position where the second radial position is radially outward of the first radial position, wherein the contact portion is in the first radial position during introduction of the device into the body of the patient and is in the second radial position during compression of the uterus of the patient between the contact portion and an applied force external of the body.

In certain embodiments, the device includes a collection reservoir, and the method further comprises collecting fluid from the patient in the collection reservoir.

In certain embodiments, the device includes one or more conduits, and the method further comprises channeling fluid from the patient out of the body.

In certain embodiments, the device includes a limiting feature for limiting the maximum insertion depth of the device in the body of the patient, and the step of introducing the device into the body of a patient comprises inserting the device into a cavity of the patient until the limiting feature prevents further insertion.

In certain embodiments, the limiting feature comprises a projecting portion extending radially outward from the at least one elongate handle at a predetermined distance from the contact portion, wherein the predetermined distance determines the maximum insertion depth of the device in the cavity where the opening of the cavity has a radius smaller than the radial extent of the projecting portion.

In certain embodiments, the step of introducing the device into the body of a patient comprises inserting the device into the vagina of the patient.

BRIEF DESCRIPTION OF THE DRAWINGS

Embodiments of the disclosure are further described hereinafter with reference to the accompanying drawings, in which.

DETAILED DESCRIPTION

Figure 1:
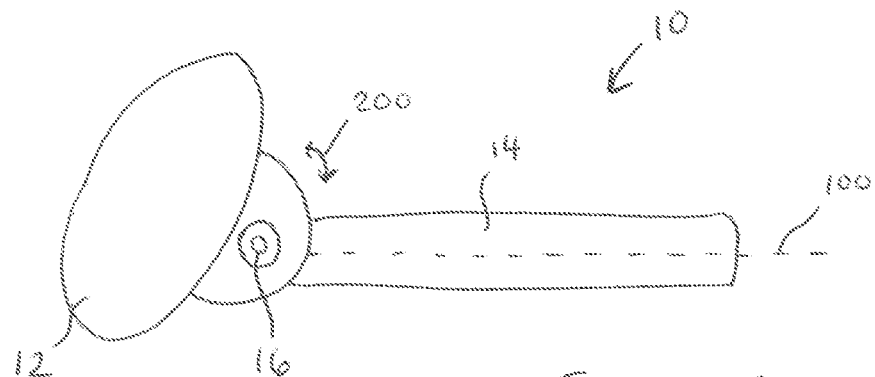
FIG. 1 shows a device in accordance with an embodiment of the present disclosure.

FIG. 1 shows a device 10 for applying a compressive force to the uterus in accordance with an embodiment of the present disclosure. The device 10 has a contact portion 12 that is configured for contacting and providing a compressive force to the uterus. Additionally, the device 10 has an elongate handle 14 connected to the contact portion 12 and extending therefrom along a longitudinal axis 100. The elongate handle 14 facilitates insertion of the device 10 into the body and handling of the device 10 in use, and is configured to transmit a force applied by the user of the device 10 to the contact portion 12 so as to apply a compressive force to the uterus. As such, the device 10 is particularly suitable for use in bi-manual compression of the uterus when managing a postpartum haemorrhage (PPH). In such circumstances, the uterus may be compressed between the contact portion 12 and a hand or other object external to the patient's body. The contact portion 12 may be any suitable surface having a surface area capable of imparting a compressive force to the uterus without causing rupturing of the tissue of the uterus.

In the non-limiting embodiment shown in FIG. 1, the device 10 further includes a pivot 16 that pivotally connects the handle 14 to the contact portion 12. The pivot 16 permits the contact portion 12 to rotate along direction 200 relative to the handle 14 and longitudinal axis 100. Thus, the contact portion 12 can move so as to vary its radial distance from the longitudinal axis 100 and may therefore move to a position relative to the handle 14 in which the device 10 may be more easily and comfortably be inserted into the patient's vagina to access the uterus. The present disclosure encompasses devices that include any means or mechanism capable of permitting at least part of the contact portion 12 to move between a first radial position and a second radial position relative to the longitudinal axis 100 where the second radial position is radially outward of the first radial position relative to the longitudinal axis 100. The change in radial position may be achieved by a rotation or linear movement (e.g. telescoping components). Nevertheless, in accordance with other embodiments within the scope of the present disclosure, the contact portion 12 may not be radially moveable relative to the longitudinal axis 100. The handle 14 may be shaped to facilitate the manual handling and grip of the handle 14, or facilitate stabilization of the device 10 against a nearby surface, for example a bed.

Figure 2:
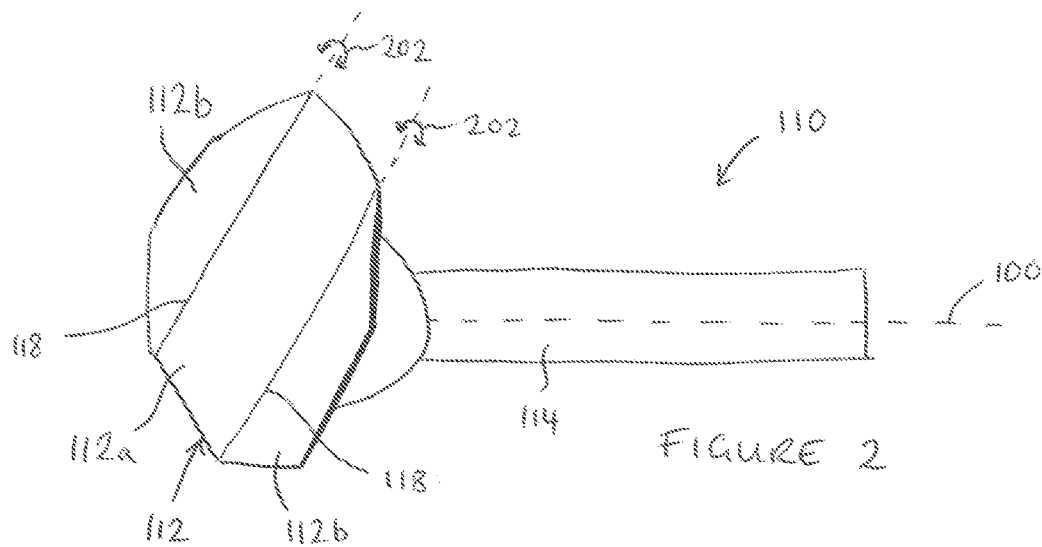
FIG. 2 shows a device in accordance with an alternative embodiment of the present disclosure.

FIGS. 2 to 6 illustrate further embodiments within the scope of the present disclosure. In particular, FIG. 2 shows a device 110 that is largely analogous to the device 10 of FIG. 1. Like the device 10 of FIG. 1, the device 110 of FIG. 2 includes a contact portion 112 and an elongate handle 114 extending away from the contact portion 112 along the longitudinal axis 100. Unlike the device 10 of FIG. 1, the contact portion 112 of the device 110 of FIG. 2 is rigidly attached to the handle 114 such that the contact portion 112 is not able to move relative to the handle 114. The contact portion 112 includes a central portion 112a and a pair of wing portions 112b extending from the central portion 112a. Each of the wing portions 112b is attached to the central portion 112a by a hinge 118 that may be formed as a living hinge. The hinges 118 permit the most radially outward parts of the wing portions 112b of the contact portion 112 to move to more radially inward positions (relative to the longitudinal axis 100) by each moving along directions 202. This movement may permit the device 110 to collapse to a configuration that facilitates easier and more comfortable insertion of the device 110.

Figure 3:
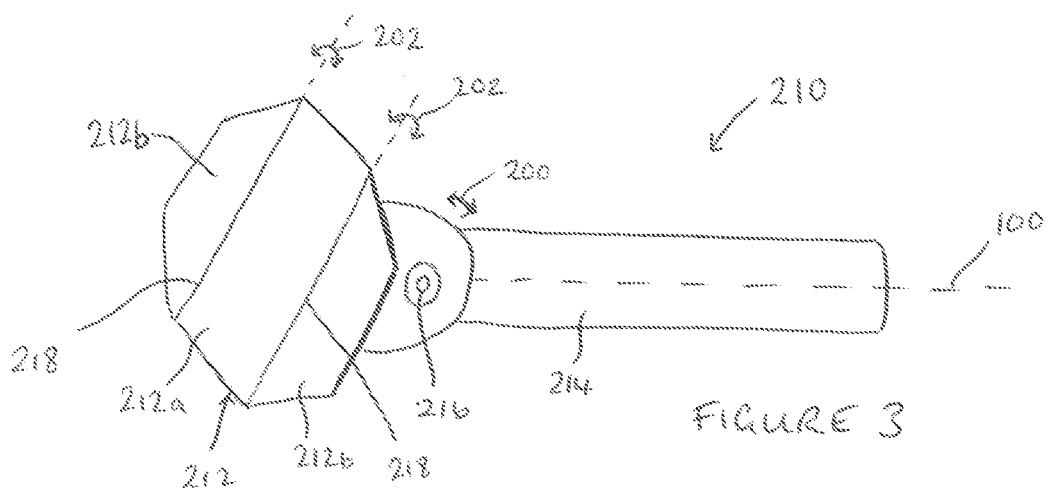
FIG. 3 shows a device in accordance with a further alternative embodiment of the present disclosure.

FIG. 3 shows a device 210 that has a contact portion 212 and an elongate handle 214 extending therefrom along the longitudinal axis 100. The handle 214 is pivotally connected to the contact portion 212 by a pivot 216 to permit pivoting of the whole of the contact portion 212 along direction 200. Additionally, the contact portion 212 includes a central contact portion 212a and wing portions 212b that are each connected to the central portion 212a by hinges 218. Therefore, the device 210 of FIG. 3 includes two distinct mechanisms by which it may be collapsed to a more radially compact configuration that facilitates easier insertion of the device 210 (i.e. movement of the contact portion along direction 200 and movement of the wing portions 212b along directions 202).

Figure 4:
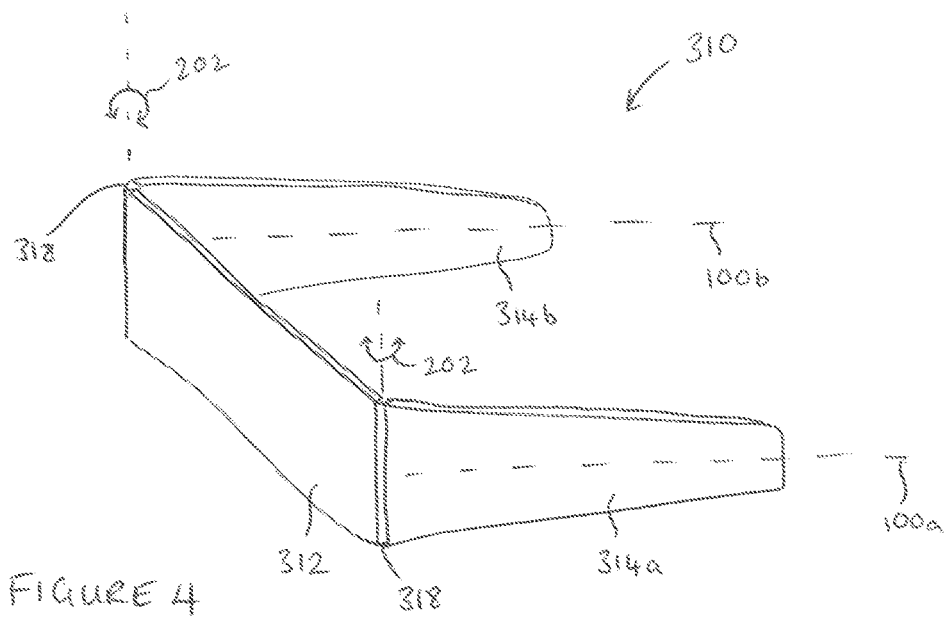
FIG. 4 shows a device in accordance with a further alternative embodiment of the present disclosure.

FIG. 4 shows a further alternative embodiment of the present disclosure. FIG. 4 shows a device 310 that is formed as a continuous elongate element that includes two hinges 318 spaced from one another. The hinges 318 define a contact portion 312, a first elongate handle 314a extending along a first longitudinal axis 100a and a second elongate handle 314b extending along a second longitudinal axis 100b. The contact portion may take any suitable shape including the elongate shape shown in FIG. 4, or the oval shape shown in FIGS. 7 and 8 (discussed in more detail below). By virtue of the hinges 318, the contact portion 312 is moveable along directions 202 shown in FIG. 4 relative to the first and second elongate handles 314a,314b. The hinges 318 may be formed as living hinges such that the device 310 may be formed as a single piece not requiring assembly (e.g. a single molding).

Figure 5:
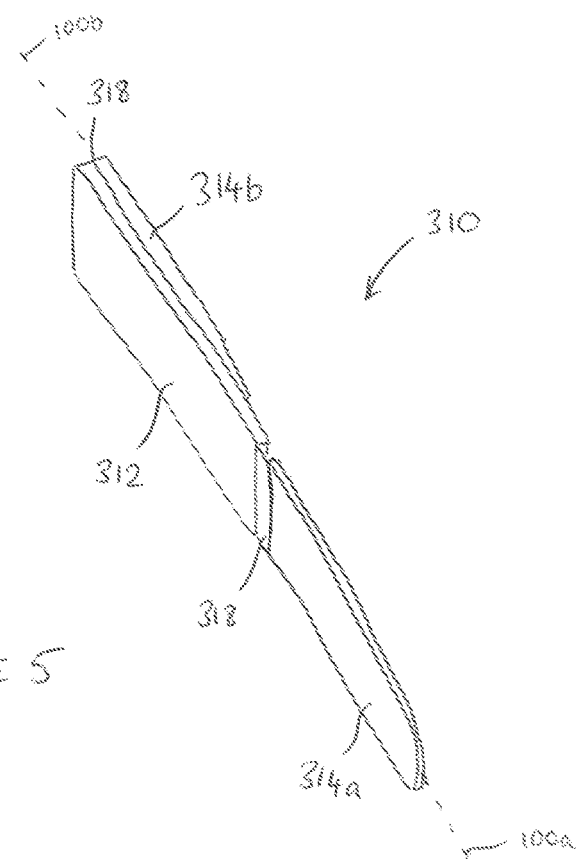
FIG. 5 shows the device of FIG. 4 in a configuration suitable for insertion into the body.

FIG. 5 shows the device 310 of FIG. 4 in a collapsed configuration that would facilitate easier and more comfortable insertion of the device 310 into the patient's body. In particular, the contact portion 312 has been moved along directions 202 (in comparison with the configuration shown in FIG. 4) so as to move to a position that is more radially inward relative to each of the first and second longitudinal axes 100a,100b. Once inserted in a cavity, the device 310 may be opened once more so as to bring the contact portion 312 into contact with the uterus to apply a compressive force thereto. In particular, in use, the first elongate handle 314a may be inclined relative to the second elongate handle 314b in a triangular formation so that the first elongate handle 314a and second elongate handle 314b may protrude from the vagina to facilitate handling of the device and application of a compressive force.

Figure 6:
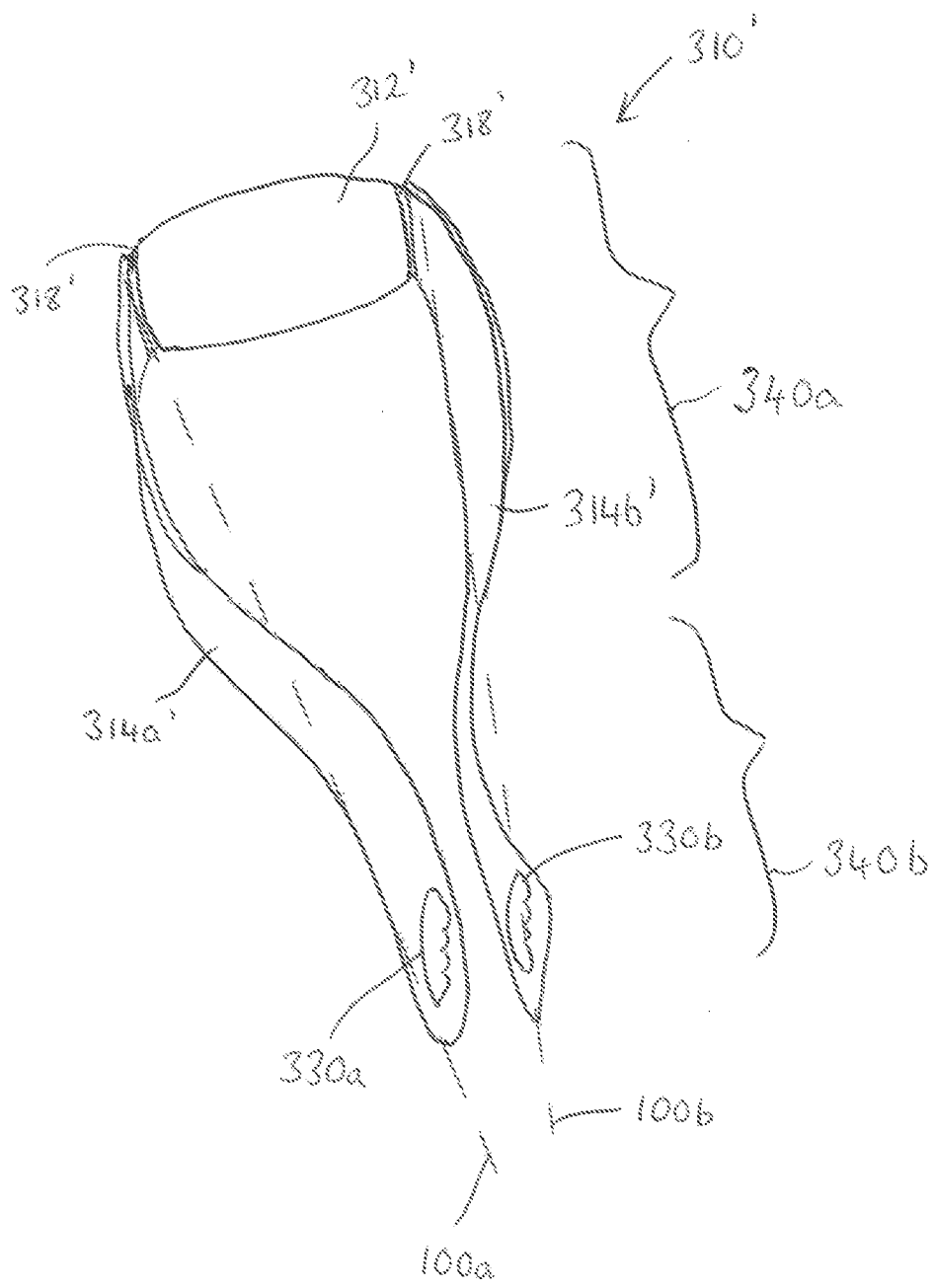
FIG. 6 shows a device in accordance with a further alternative embodiment of the present disclosure.

FIG. 6 shows a device 310' similar to that shown in FIGS. 4 and 5. The device 310' includes a contact portion 312' with a first elongate handle 314a' and a second elongate handle 314b' extending therefrom. Each of the first elongate handle 314a' and the second elongate handle 314b' extends generally along a respective longitudinal axis 100a,100b. In addition, the first elongate handle 314a' and second elongate handle 314b' undulate radially along their respective longitudinal lengths (indeed, the one or more elongate handles in any of the embodiments within the scope of the present disclosure may undulate in this manner). The first elongate handle 314a' and second elongate handle 314b' may additionally have a curved or angled profile in a cross sectional plane that is orthogonal to the respective longitudinal axis 100a,100b. Such a curved profile may provide each of the first elongate handle 314a' and second elongate handle 314b' with the required strength characteristics whilst requiring an economical amount of material for its formation.

The contact portion 312' is hingedly connected to the first elongate handle 314a' and second elongate handle 314b' by hinges 318' which may be living hinges or other suitable hinge components. Due to the undulating profile of the first elongate handle 314a' and second elongate handle 314b' along the longitudinal axes 100a,100b, the first elongate handle 314a' and second elongate handle 314b' define a wide portion 340a and a narrow portion 340b. The wide portion 340a may accommodate a fluid reservoir (e.g. a bag) that is connected to the contact surface 312' and is arranged to collect fluid (e.g. uterine blood). The narrow portion 340b allows the ends of the first elongate handle 314a' and second elongate handle 314b' that are remote from the contact portion 312' to pass through the opening of the vagina and permit the device 310' to be handled and controlled with minimal discomfort to the patient. Preferably, the narrow portion 340b is such that the first elongate handle 314a' and second elongate handle 314b' may contact one another. In the non-limiting embodiment shown in FIG. 6, the first elongate handle 314a' and second elongate handle 314b' include handle holes 330a,330b respectively that permit the user to grip both of the first elongate handle 314a' and second elongate handle 314b' with a single hand when the first elongate handle 314a' and second elongate handle 314b' are brought together at the narrow portion 340b. In any embodiment in accordance with the present disclosure, the one or more elongate handles may include handle holes or any other suitable feature that facilitates improved handling, gripping or manipulation of the device.

In any embodiment, the device may include a limiting feature that serves to guide and limit the maximum insertion depth of the device in a cavity (e.g. the vagina) which could lead to discomfort or damage. The limiting feature may be a projecting portion that extends radially outwardly from the elongate handle so as to prevent over insertion of the device. In particular embodiments, the projecting portion may be a flange that extends around the elongate handle.

In certain circumstances, it may be desirable to collect or channel fluid from the uterus. For example, uterine blood may be collected or channeled. Therefore, in certain embodiments, the device may include means to collect or channel fluid. In particular, the contact portion may be configured to permit the passage of fluid therethrough. The contact portion may have holes or apertures that allow the passage of fluid, or a permeable material may be present. The device may include a collection reservoir (e.g. a flexible bag) for collecting fluid. Additionally or alternatively, the device may include one or more conduits for channeling fluid away from the uterus. Such one or more conduits may pass alongside or through the elongate handle and out of the device to an external collector.

The device may include one or more mechanical or electrical sensors or indicators. For example, indicators may be present that measure the pressure or force being applied by the device against a surface to guide appropriate and effective use of the device. The sensors or indicators may form part of the elongate handle or the contact portion. In certain examples, the indicator may include a compressible member such as a spring that provides an indication of the force being applied by the device. In other examples, the indicators or sensors may measure physiological parameters associated with the patient.

The surface of the contact portion may be planar or may be concave or any other suitable shape in order to provide the desired contact with the uterus. In certain embodiments, the contact portion may have a surface that is concave relative two orthogonal axes (e.g. horizontal and vertical) across the face of the surface.

In certain preferable embodiments, the device may include releasable locking means that temporarily lock the device in its force applying configuration so that the risk of undesirable radial movement of the contact portion (or, at least, part of the contact portion) is minimized.

Figure 7:
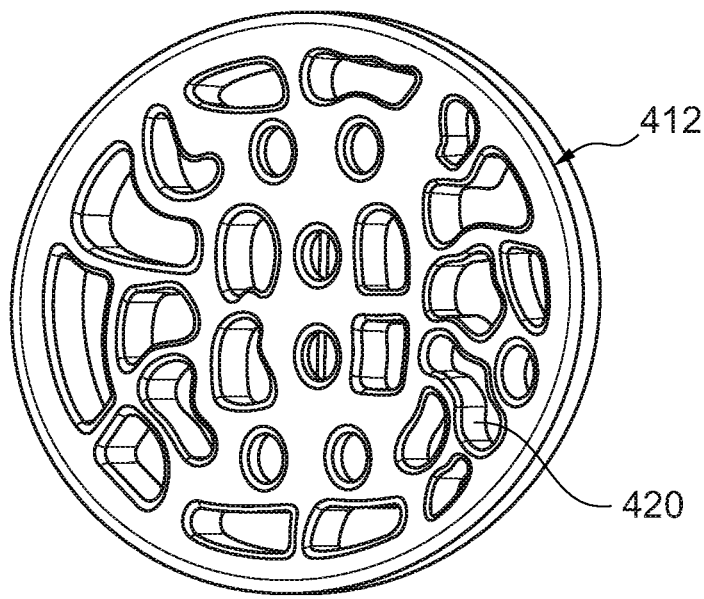
FIG. 7 shows a front view of contact portion in accordance with a specific embodiment of the present disclosure.
Figure 8:
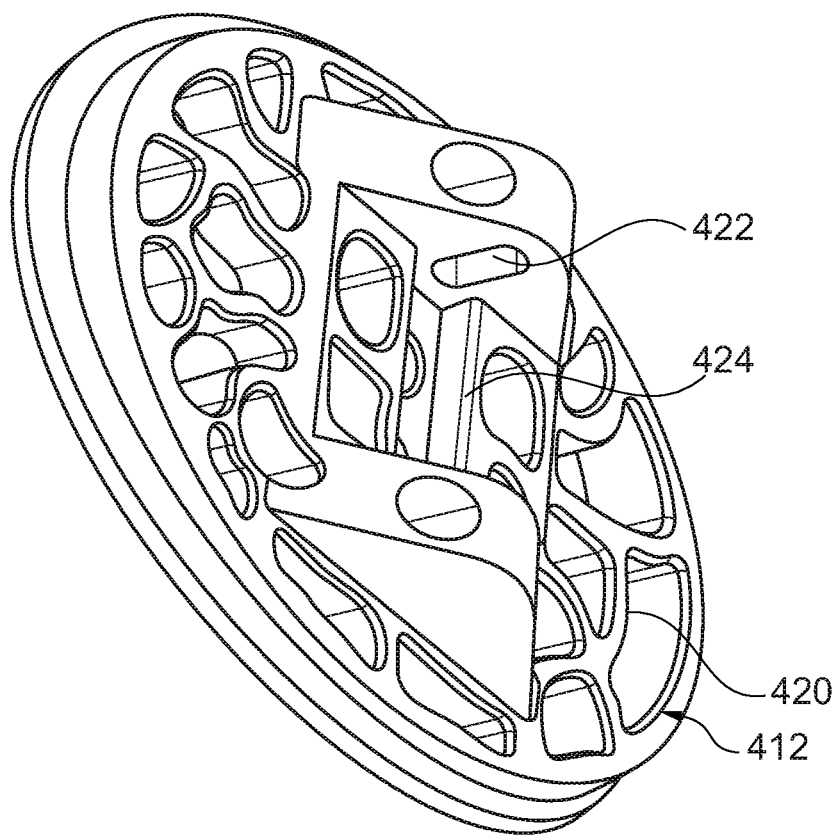
FIG. 8 shows a rear view of the contact portion of FIG. 7.

A specific embodiment of a contact portion 412 in accordance with the present disclosure is shown in FIGS. 7 and 8 where FIG. 7 shows a front view of the contact portion 412 and FIG. 8 shows a rear view of the contact portion 412. The contact portion 412 includes a plurality of holes 420 that provide fluid pathways from the front on the contact portion 412 to the rear of the contact portion 412. The holes 420 may permit the passage of fluid such as uterine blood for collection or channeling rearward of the contact portion 412. A bag or other suitable reservoir may be arranged rearward of the contact portion 412 to collect fluid passing through the plurality of holes 420. The front surface of the contact portion 412 is generally concave (notwithstanding the presence of the holes 420). The surfaces and edges of the contact portion are rounded and smooth so as to minimize any tissue damage when compressed against the uterus. In certain embodiments, the contact portion 412 (e.g. its rear surface) may include one or more lights to facilitate the visualization of the interior of the vagina and thus enable an assessment of lacerations or trauma.

The rear of the contact portion 412 includes pivot slots 422 for receiving an axle that may pass through an elongate handle (or a component intermediate the contact portion 412 and elongate handle) and permit rotational movement of the contact portion 412 relative to the elongate handle. Additionally, the rear surface of the contact portion 412 includes a channel 424 with a square profile that is configured to receive a correspondingly shaped part of the elongate handle. When the correspondingly shaped part of the elongate handle is engaged in the channel 424, the possibility of rotation of the contact portion 412 relative to the elongate handle is minimized due to mechanical interference with the channel 424, and so a force may be applied to the uterus by the device with minimal risk that the contact portion 412 will rotate (i.e. towards a collapsed configuration for insertion or removal). Nevertheless, due to the elongate nature of the pivot slots 422, the elongate handle may be moved away from the channel 424 so as to permit rotation of the contact portion 412 relative to the elongate handle when it is desired to rotate the contact portion 412 relative to the elongate handle and associated longitudinal axis (e.g. when moving the device to a collapsed configuration for insertion or removal). In alternative embodiments, any other suitably shaped channel (and correspondingly shaped part of the elongate handle) may facilitate the selective locking of the elongate handle relative to the contact portion.

Figure 9:
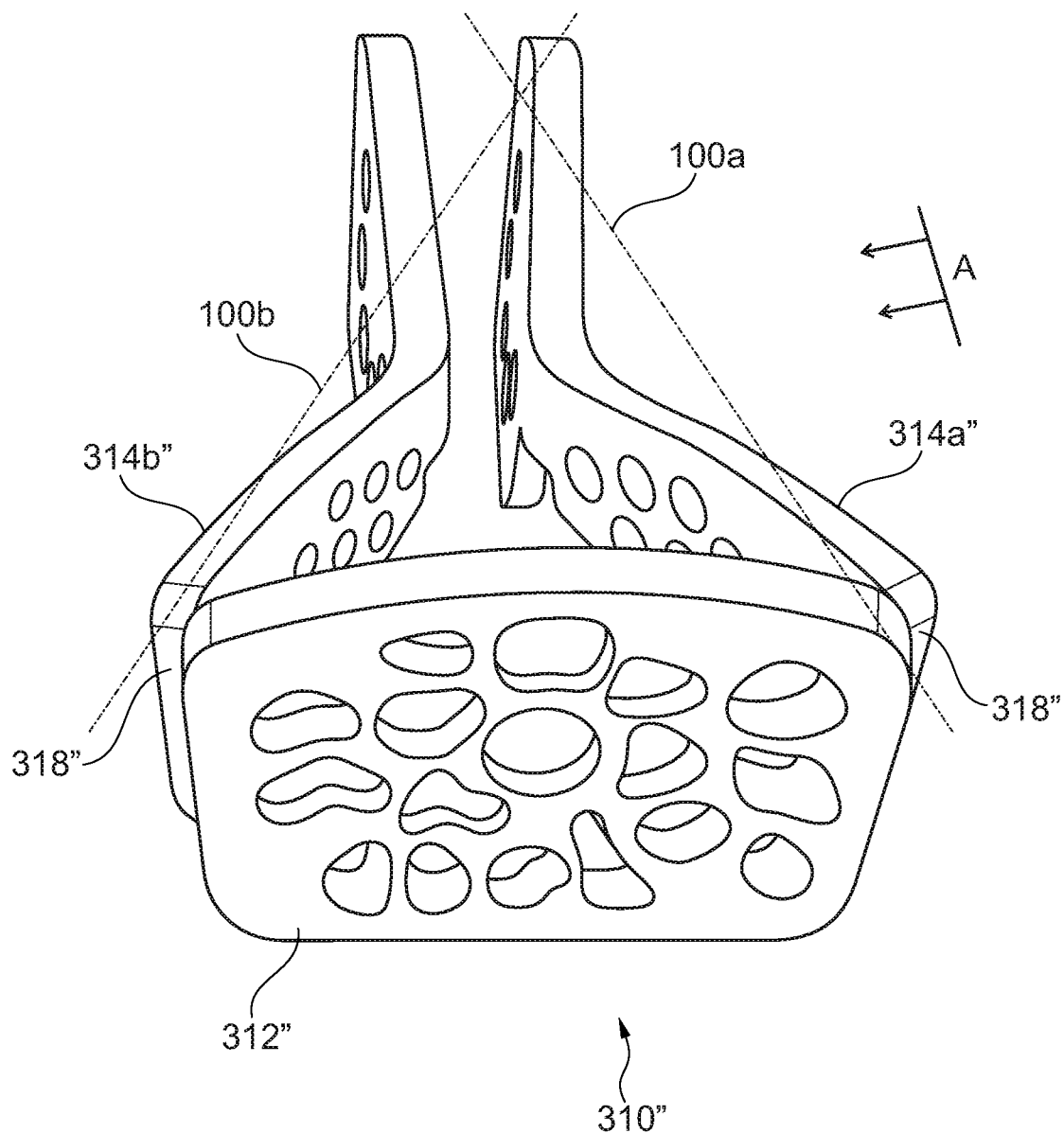
FIG. 9 shows a device in accordance with a further alternative embodiment of the present disclosure.
Figure 10:
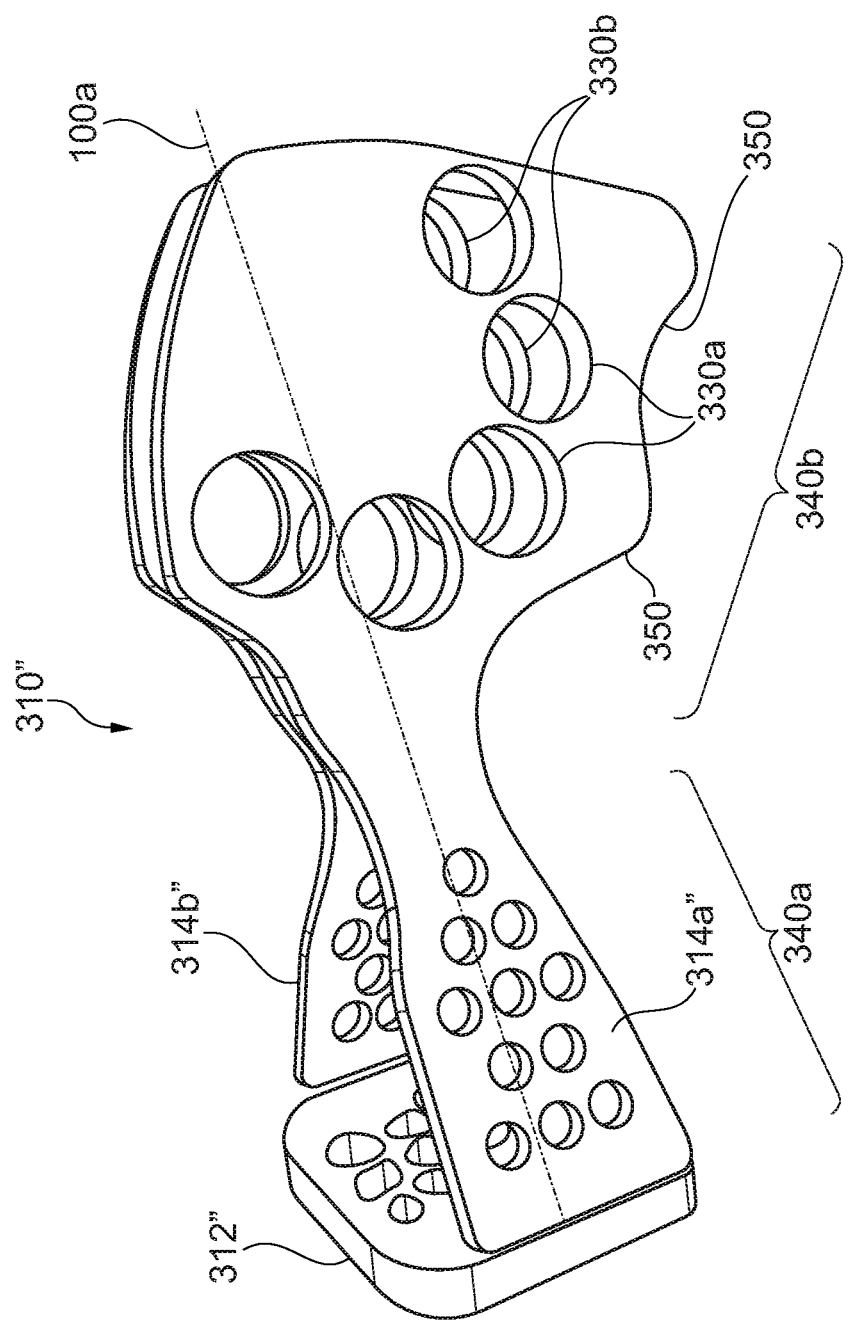
FIG. 10 shows the device of FIG. 9 shown from position A indicated on FIG. 9.

FIGS. 9 and 10 show a device 310" similar to that shown in FIG. 6. The device 310" includes a contact portion 312" with a first elongate handle 314a" and a second elongate handle 314b" extending therefrom. Each of the first elongate handle 314a" and the second elongate handle 314b" extends generally along a respective longitudinal axis 100a,100b. In addition, the first elongate handle 314a" and second elongate handle 314b" undulate radially along their respective longitudinal lengths like the embodiment of FIG. 6.

The contact portion 312" is hingedly connected to the first elongate handle 314a" and second elongate handle 314b" by hinges 318" which may be living hinges or other suitable hinge components. Due to the undulating profile of the first elongate handle 314a" and second elongate handle 314b" along the longitudinal axes 100a,100b, the first elongate handle 314a" and second elongate handle 314b" define a wide portion 340a and a narrow portion 340b as shown in FIG. 10. The wide portion 340a may accommodate a fluid reservoir (e.g. a bag) that is connected to the contact surface 312" and is arranged to collect fluid (e.g. uterine blood). The narrow portion 340b allows the ends of the first elongate handle 314a" and second elongate handle 314b" that are remote from the contact portion 312" to pass through the opening of the vagina and permit the device 310" to be handled and controlled with minimal discomfort to the patient. Preferably, the narrow portion 340b is such that the first elongate handle 314a" and second elongate handle 314b" may contact one another. Further preferably, the first elongate handle 314a" is releasably lockable to the second elongate handle 314b" in the narrow portion 340b to temporarily lock the device 310" in its force applying configuration so that the risk of undesirable radial movement of the contact portion 312" (or, at least, part of the contact portion) is minimized. The locking mechanism may be such that the locking of the first elongate handle 314a" to the second elongate handle 314b" may also indicate to the user that the first elongate handle 314a" is correctly aligned with the second elongate handle 314b" for applying a force to the uterus. The first elongate handle 314a" and second elongate handle 314b" include handle holes 330a,330b respectively that permit the user to grip both of the first elongate handle 314a" and second elongate handle 314b" with a single hand when the first elongate handle 314a" and second elongate handle 314b" are brought together at the narrow portion 340b. Unlike the handle holes 330a,330b of the embodiment of FIG. 6, the handle holes 330a,330b of the embodiment of FIGS. 9 and 10 are each provided as a plurality of holes for receiving individual fingers of the user. The handle holes 330a are aligned with the handle holes 330b when the first elongate handle 314a" is aligned with the second elongate handle 314b" so that both of the first elongate handle 314a" and the second elongate handle 314b" can be gripped with the same hand. Furthermore, by passing a single hand (or, for example, individual fingers) through the aligned handle holes 330a,330b, the first elongate handle 314a" and the second elongate handle 314b" may be maintained in an aligned configuration thereby further minimising the risk of undesirable radial movement of the contact portion 312".

Additionally, the first elongate handle 314a" and second elongate handle 314b" are each provided with radial projections 350 on a lower surface. Two such radial projections 350 are shown projecting radially (i.e. perpendicularly to longitudinal axis 100a) from the first elongate handle 314a". The radial projections 350 may assist in anchoring the device 310" during application of a force. For example, the radial projections 350 may bite into a soft surface (such as the patient's bed) when a force is applied to the patient's uterus with the device 310". The radial projections 350 may therefore maintain alignment and prevent unwanted movement of the device 310" during use. In particular, the radial projections 350 may improve the ease of use of the device 310" and improve the capability of the device 310" to transfer a force to the uterus. Any number of radial projections 350 may be provided in any embodiment within the scope of the present disclosure.

A preferred method of using a device in accordance with the present disclosure is described below.

Firstly, the device may be removed from any packaging. The device may then be lubricated using a lubricant such as obstetric cream or aqueous gel. Vaginal clots may be expelled by application of a force (e.g. by hand) on the fundus of the uterus. Next, the device is suitably orientated for insertion. In embodiments where at least a part of the contact portion is configured to be radially moveable relative to the longitudinal axis, the at least part of the contact portion may be moved to a radially inward position relative to the longitudinal axis. The device is then inserted into the vagina. Where a limiting feature is present, insertion may continue until the insertion feature contacts the opening of the vagina. In embodiments where a fluid collection reservoir or one or more conduits are present, it is preferable to ensure that these are orientated to permit the free flow of fluid thereinto or therethrough. Once the device is inserted, the device may be orientated for the application of a force to the uterus, where the contact portion contacts the uterus. In embodiments where at least a part of the contact portion is configured to be radially moveable relative to the longitudinal axis, the at least part of the contact portion may be moved to a radially outward position relative to the longitudinal axis. The uterus may then be compressed between the contact portion and a hand (or other surface) placed externally on the fundus of the uterus, with the device being held in place during use. If uterine compression is found not to stop the bleeding, it is likely that the bleeding is coming from lacerations which may be in the perineum, vagina or cervix. In this case, the device may be removed and the lacerations may be repaired. If, however, the bleeding is found to cease with uterine compression, it may be preferable to continue uterine compression for a further time period (e.g. for around 5 minutes). Following this time period, the compressive force may be removed and a check may be performed to assess whether bleeding recommences. In embodiments where a fluid reservoir or conduit is present, uterine blood flow may be monitored by inspection of blood passing into the reservoir or through the conduit. If bleeding is found to recommence following removal of the compression, compression of the uterus may be repeated and further oxytocics may be given. Compression and assessment of bleeding when compression is removed may be repeated until bleeding ceases. Once bleeding has stopped following removal of compression, the device may be orientated appropriately for easier and more comfortable removal and the device may be removed. The device may then be disposed of.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

The invention claimed is:

1. A device for applying a compressive force to the uterus so that the uterus can be compressed between the device and an applied force external of the body to treat postpartum hemorrhage, the device comprising:
   a contact portion for contacting the uterus and providing a compressive force thereto, the contact portion having a surface area capable of imparting the compressive force to the uterus without perforating or causing trauma to the tissue of the uterus and comprising a plurality of holes that provide fluid pathways from a front of the contact portion to a rear of the contact portion, and
   at least two elongate handles each extending from the contact portion along a respective longitudinal axis, wherein each of the at least two elongate handles is a unitary component and is sufficiently rigid to facilitate insertion of the device into the body through the vagina and handling of the device from outside the body when inserted, each of the at least two elongate handles comprising a first portion and a second portion, the first portion of each elongate handle configured to be manipulated by a user from outside the body to transmit a force directly applied by the user via the first portion of each elongate handle to the contact portion once the contact portion and the second portion of each elongate handle have been inserted through the vagina so as to apply a compressive force to the uterus;

wherein the at least two elongate handles permit the user to grip both of the at least two elongate handles at their respective first portions with a single hand when the first portions of the at least two elongate handles are brought together; and wherein at least a part of the contact portion is configured to be radially moveable relative to the longitudinal axes between a first radial position and a second radial position where the second radial position is radially outward of the first radial position, wherein when the contact portion is in the first radial position the device is in a more radially compact configuration that facilitates easier and more comfortable insertion of the device into the body relative to when the contact portion is in second radial position.

2. The device of claim 1, wherein the contact portion is pivotally mounted so as to be radially moveable relative to the longitudinal axes.

3. The device of claim 2, wherein the contact portion is pivotally mounted to the at least two elongate handles.

4. The device of claim 1, wherein the at least part of the contact portion is rotatable relative another part of the contact portion and the longitudinal axes.

5. The device of claim 4, wherein said at least part of the contact portion is connected to another part of the contact portion by a first hinge.

6. The device of claim 5, wherein said first hinge is a living hinge.

7. The device of claim 1, wherein the contact portion is connected to the at least one elongate handle by a handle hinge.

8. The device of claim 7, wherein the handle hinge is a living hinge.

9. The device of claim 1, wherein the device is formed as a continuous elongate element that includes two living hinges spaced from one another thereby defining the contact portion that is hingedly connected to two elongate handles extending from the contact portion.

10. The device of claim 1, further including a limiting feature for limiting the maximum insertion depth of the device in a cavity.

11. The device of claim 10, wherein the limiting feature comprises a projecting portion extending radially outward from one or more of the at least two elongate handles at a predetermined distance from the contact portion, wherein the predetermined distance determines the maximum insertion depth of the device in a cavity where the opening of the cavity has a radius smaller than the radial extent of the projecting portion.

12. The device of claim 11, wherein the projecting portion is a flange that is substantially circumferentially continuous about the at least one elongate handle.

13. The device of claim 1, further including a collection reservoir for receiving fluid that passes through the contact portion.

14. The device of claim 1, further including one or more sensors or indicators for measuring pressure applied by the device against a surface.

15. The device of claim 14, wherein the one or more sensors or indicators forms part of the contact portion.

16. The device of claim 14, wherein the one or more sensors or indicators forms part of the at least one elongate handle.

17. The device of claim 14, wherein the one or more sensors or indicators include a mechanical indicator.

18. The device of claim 17, wherein the mechanical indicator includes a compressible member.

19. The device of claim 18, wherein the compressible member is a spring.

20. The device of claim 14, wherein the one or more sensors or indicators include an electronic sensor.

21. The device of claim 1, wherein the contact surface is a substantially planar surface.

22. The device of claim 1, wherein the contact portion is concave.

23. A method for treating postpartum hemorrhage, comprising:
   introducing the device of claim 1 into the body of a patient; and
   compressing the uterus of the patient against the contact portion.

24. The method of claim 23, wherein the step of compressing the uterus of the patient against the contact portion includes applying a force external of the body to the at least two elongate handles.

25. The method of claim 24, wherein the contact portion is in the first radial position during introduction of the device into the body of the patient and is in the second radial position during compression of the uterus of the patient against the contact portion.

26. The method of claim 23, wherein the device includes a collection reservoir, and the method further comprises collecting fluid from the patient in the collection reservoir.

27. The method of claim 23 wherein the device includes one or more conduits, and the method further comprises channeling fluid from the patient out of the body.

28. The method of claim 23, wherein the device includes a limiting feature for limiting the maximum insertion depth of the device in the body of the patient, wherein the step of introducing the device into the body of a patient comprises inserting the device into a cavity of the patient until the limiting feature prevents further insertion.

29. The method of claim 28, wherein the limiting feature comprises a projecting portion extending radially outward from the at least two elongate handles at a predetermined distance from the contact portion, wherein the predetermined distance determines the maximum insertion depth of the device in the cavity where the opening of the cavity has a radius smaller than the radial extent of the projecting portion.

30. The method of claim 23, wherein the step of introducing the device into the body of a patient comprises inserting the device into the vagina of the patient.

* * * * *